(12) United States Patent
Lopa et al.

(10) Patent No.: US 11,221,292 B2
(45) Date of Patent: Jan. 11, 2022

(54) METHOD UTILIZING IN-SITU, SUBSURFACE, NEAR-INFRARED SPECTROSCOPY TO DETECT BURIED HUMAN REMAINS

(71) Applicants: Afrin Lopa, Cuyahoga Falls, OH (US); David Perry, Akron, OH (US); Timothy Matney, Akron, OH (US); Linda Barrett, Fairlawn, OH (US)

(72) Inventors: Afrin Lopa, Cuyahoga Falls, OH (US); David Perry, Akron, OH (US); Timothy Matney, Akron, OH (US); Linda Barrett, Fairlawn, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 16/901,305

(22) Filed: Jun. 15, 2020

(65) Prior Publication Data
US 2020/0393369 A1 Dec. 17, 2020

Related U.S. Application Data

(60) Provisional application No. 63/033,934, filed on Jun. 3, 2020, provisional application No. 62/861,492, filed on Jun. 14, 2019.

(51) Int. Cl.
*G01N 21/359* (2014.01)
*G01V 8/10* (2006.01)
(Continued)

(52) U.S. Cl.
CPC ....... *G01N 21/359* (2013.01); *G01N 21/3563* (2013.01); *G01N 33/246* (2013.01); *G01V 8/10* (2013.01)

(58) Field of Classification Search
CPC ............ G01N 21/359; G01N 21/3563; G01N 33/246; G01V 8/10
See application file for complete search history.

(56) References Cited

U.S. PATENT DOCUMENTS 5,038,040 A  8/1991 Funk et al.
5,461,229 A  10/1995 Sauter et al.
(Continued)

OTHER PUBLICATIONS

Notter, Stephanie J., et al. "The initial changes of fat deposits during the decomposition of human and pig remains." Journal of Forensic Sciences 54.1 (2009): 195-201. (Year: 2006).*
(Continued)

*Primary Examiner* — Dominic J Bologna
(74) *Attorney, Agent, or Firm* — Renner Kenner Greive Bobak Taylor & Weber

(57) ABSTRACT

A method for locating human remains in a clandestine or undocumented burial includes providing a spectroscopy assembly including a spectroscopy probe with a distal end to a location that may include human remains, wherein the spectroscopy assembly is configured to identify whether a salt of a fatty acid is present based on overtone wavelengths of the salt of the fatty acid; inserting the distal end of the spectroscopy probe into a testing spot at the location that may include human remains; and analyzing, with the spectroscopy assembly and after the step of inserting, whether the salt of the fatty acid having the overtone wavelengths is present in the location that may include human remains. The step of analyzing may include near-infrared spectroscopy, and the overtone wavelengths may be characterized by an absorption band contour extending from about 1670 nm to about 1800 nm.

20 Claims, 3 Drawing Sheets

(51) Int. Cl.
    *G01N 33/24*     (2006.01)
    *G01N 21/3563*     (2014.01)

(56) References Cited

U.S. PATENT DOCUMENTS

| | | | |
|---|---|---|---|
| 9,285,501 B2 | 3/2016 | Christy et al. | |
| 2011/0106451 A1* | 5/2011 | Christy | G01N 21/8507 702/5 |
| 2017/0370064 A1* | 12/2017 | Morgan | G01J 3/0208 |

OTHER PUBLICATIONS

Rossel, RA Viscarra, et al. "In situ measurements of soil colour, mineral composition and clay content by vis-NIR spectroscopy." Geoderma 150.3-4 (2009): 253-266. (Year: 2009).*

Forbes, Shari L., Boyd B. Dent, and Barbara H. Stuart. "The effect of soil type on adipocere formation." Forensic science international 154.1 (2005): 35-43. (Year: 2005).*

Bereuter, Thomas L., Werner Mikenda, and Christian Reiter. "Iceman's Mummification—Implications from Infrared Spectroscopical and Histological Studies." Chemistry—A European Journal 3.7 (1997): 1032-1038. (Year: 1997).*

53. Stuart, B. H., et al. "Studies of adipocere using diffuse reflectance infrared spectroscopy." Vibrational Spectroscopy 24.2 (2000): 233-242 (Year: 2000).*

Merriam-Webster.com Dictionary, Merriam-Webster, https://www.merriam-webster.com/dictionary/human%20remains. Accessed Aug. 19, 2021). (Year: 2021).*

Powell, K. "The Detection of Buried Human Skeletal Remains in The Australian Environment" Department of Anatomical Sciences, University of Adelaide, Apr. 2006. (Year: 2003).*

Surabian, "Preservation of Buried Human Remains in Soil", U.S. Department of Agriculture Natural Resources Conservation Service, Dec. 2012 (Year: 2012).*

Miller et al. "Cemetery Setback Distances To Prevent Surface Water Contamination" Oct. 2017, National Collaborating Centre for Environmental Health (Year: 2017).*

* cited by examiner

METHOD UTILIZING IN-SITU, SUBSURFACE, NEAR-INFRARED SPECTROSCOPY TO DETECT BURIED HUMAN REMAINS

CROSS REFERENCE TO RELATED APPLICATIONS

This application claims the benefit of U.S. provisional patent application Ser. No. 62/861,492, filed Jun. 14, 2019, and of U.S. provisional patent application Ser. No. 63/033,934, filed Jun. 3, 2020, which are each incorporated by reference herein.

FIELD OF THE INVENTION

The present invention is directed to a method of locating human remains in clandestine or undocumented burials by detecting fatty acids or their salts utilizing in-situ, subsurface, near-infrared spectroscopy.

BACKGROUND OF THE INVENTION

Existing methodologies for locating human remains in clandestine or undocumented burials include cadaver dogs, ground penetrating radar, and unguided excavations. However, these methodologies suffer from various disadvantages.

Cadaver dogs, when well trained and professionally handled, signal odors that result from the presence and decomposition of the cadaver. The chemical compounds responsible for these odors are volatile and may be water-soluble. Depending on the history and drainage of the site, a cadaver dog may find such odors in many places other than where the cadaver is actually buried. In this case, the negative result is the time and expense of fruitless excavations. In other cases, with a longer post-mortem interval, the odors may no longer be detectable.

Ground penetrating radar (GPR) is capable of detecting variations in density below the surface of the soil, but GPR does not indicate the nature of what is in the ground.

And, it is of course possible to conduct excavations in search of a burial where the search is unguided by any particular means. Such unguided excavations are generally expensive, time consuming, and unsuccessful.

In addition to these techniques, other apparatuses have been used for performing geophysical surveys and testing soil properties. Some of these apparatuses found in the patent literature are introduced below.

U.S. Pat. No. 5,038,040 discloses a soil test apparatus for field use. The soil test apparatus includes means adapted for transport over a field for testing the soil thereof The soil test apparatus further includes an infrared radiation generator for producing infrared radiation at a plurality of predetermined wavelengths, an elongate light carrying member coupled to the infrared radiation generator and extending therefrom for directing infrared radiation onto the soil, and a light detector for detecting infrared radiation reflected from the soil and for producing corresponding electrical signals.

U.S. Pat. No. 5,461,229 discloses an on-the-go probe for determining the presence of chemical residue in a soil using Transient Infrared Spectroscopy. The probe pulls a soil implement through the soil and the soil implement includes a heating or cooling source for temporarily creating a temperature differential between a layer of soil proximate the soil implement and a layer of soil remote from the soil implement. The soil is moved sufficiently fast with respect to the heating source to enable measuring the radiation characteristics of the thin layer of soil before the thin layer of soil begins to self-absorb and substantially change its emission characteristics.

U.S. Pat. No. 9,285,501 discloses a multi-sensor system that measures diffuse reflectance of soil, soil conductivity, and other soil properties in situ, in three dimensions. The system includes a tractor-drawn implement containing a sensor shank used for X-Y axis measurements, a hydraulic probe implement containing a sensor probe for −Z axis measurements, and a set of visible and near-infrared spectrometers, controls, and firmware that are shared by each implement. Both implements include optical sensors and soil electrical conductivity sensors. The probe implement incorporates a sensor that measures insertion force, and the shank implement includes a soil temperature sensor. These combinations of sensors are used to calibrate the system and to characterize the soil properties within a field or area. Geo-referenced soil measurements are collected with the shank implement to identify optimal locations for conducting sensor probe insertions. The probe implement is then used for sensor probing and for collecting soil core samples for lab analysis.

However, these patents do not disclose the utilization of these apparatuses with any particular method for locating human remains in clandestine or undocumented burials. There remains a need in the art for an improved method for locating human remains in clandestine or undocumented burials.

SUMMARY OF THE INVENTION

The present invention provides a method for locating human remains in a clandestine or undocumented burial, the method including providing a spectroscopy assembly including a spectroscopy probe with a distal end to a location that may include human remains, wherein the spectroscopy assembly is configured to identify whether a salt of a fatty acid is present based on overtone wavelengths of the salt of the fatty acid; inserting the distal end of the spectroscopy probe into a testing spot at the location that may include human remains; and analyzing, with the spectroscopy assembly and after the step of inserting, whether the salt of the fatty acid having the overtone wavelengths is present in the location that may include human remains. The step of analyzing may include utilizing near-infrared spectroscopy, and the overtone wavelengths may be characterized by an absorption band contour extending from about 1670 nm to about 1800 nm.

BRIEF DESCRIPTION OF THE DRAWINGS

Advantages of the present invention will become better understood with regard to the following description, appended claims, and accompanying drawings wherein:

DETAILED DESCRIPTION OF THE ILLUSTRATIVE EMBODIMENTS

One or more embodiments of the present invention are directed to a method of locating human remains in clandestine or undocumented burials. Advantageously, methods disclosed herein utilize in-situ subsurface, near-infrared spectroscopy, and focus on certain absorption bands, where the absorption bands are particularly useful for identifying fatty acids, by way of the salts of those fatty acids, from the human remains to be located. When these characteristic absorption features are observed, this is indicative of human remains being present at that location. The methods disclosed herein may be practically implemented by inserting a probe into the soil to measure diffuse reflectance spectra. One or more embodiments of the present invention are also directed to a probe assembly system that utilizes the method of detection.

Figure 1:
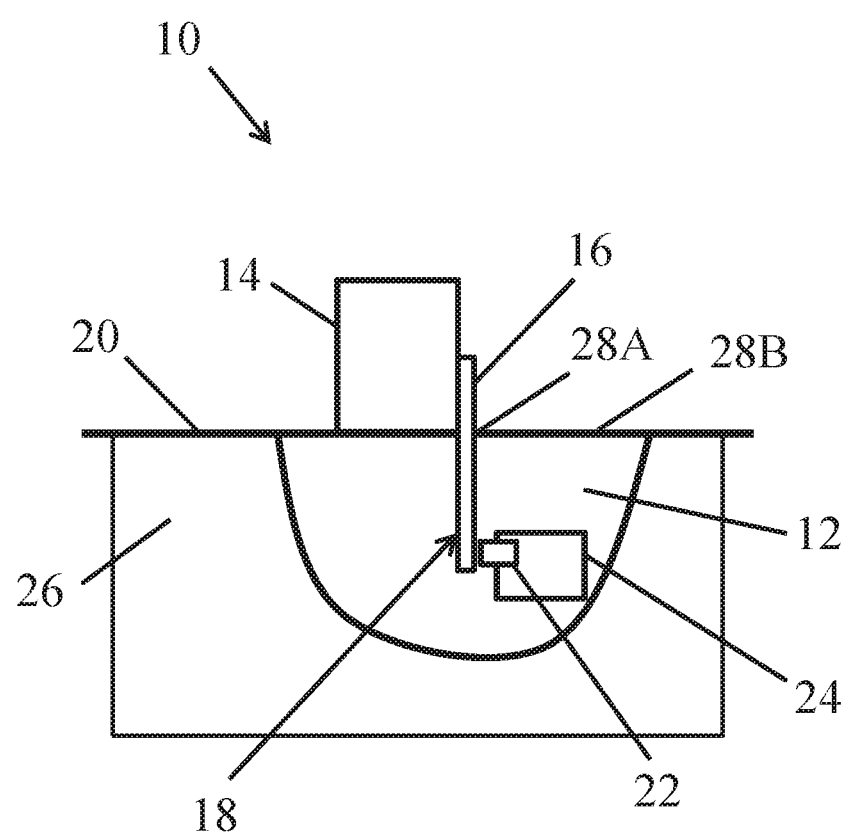
FIG. 1 is a schematic for a method according to one or more embodiments of the present invention.

Aspects of one or more embodiments of the present invention can be described with reference to FIG. 1, which shows a schematic for a method 10 of locating human remains in a clandestine or undocumented burial location 12. Clandestine or undocumented burial location 12 may also be referred to soil location 12 or location 12 that may include human remains. The method 10 may include a first step of identifying the location 12 that may include human remains.

The method 10 includes providing a spectroscopy assembly 14 that includes a spectroscopy probe 16. The spectroscopy probe 16 includes a distal end 18 to be inserted below ground level 20 and into the location 14 that may include human remains.

With distal end 18 below ground level 20 and in the location 14 that may include human remains, spectroscopy assembly 14 with spectroscopy probe 16 is utilized to perform an analysis step regarding the contents of location 12. Specifically, spectroscopy assembly 14 analyzes whether any fatty acids 22, or a salt of a fatty acid 22, are present in the location 12 that may include human remains.

Method 10 may also include additional steps toward further verification that the location 12 does indeed include human remains. These additional steps may include measuring a secondary property of the location 12 that may include human remains. As used herein, the term secondary is utilized to indicate a property or indicator in addition to the presence of the salts of fatty acids 22. The same secondary property can also be measured for a nearby location 26 that is near the location 12 that may include human remains, which may also be referred to as a background location 26. Nearby location 26 should be a location that does not include human remains, or a location that has not been disturbed in the same way that location 12 may have been disturbed. Then, the secondary property of the location 12 that may include human remains can be compared with the secondary property of the nearby location 26 that does not include human remains. As will be discussed further herein, the step of comparing is generally suitable for eliminating any false negative conclusion from the step analyzing whether the salt of the fatty acid is present, to thereby provide further conclusive results.

Practice of the present methods disclosed herein is generally not limited by the utilization of any particular spectroscopy assembly 14. Suitable spectroscopy assembly 14 and spectroscopy probe 16 are generally known to the skilled person.

Spectroscopy assembly 14 may be referred to as a push-probe system 14. Spectroscopy assembly 14 includes the ability to perform near-infrared spectroscopy and may also include the ability to perform visible spectroscopy and other potentially useful spectroscopy.

Spectroscopy probe 16 may include a small window through which light passes. The window may be made from sapphire or diamond. When in the ground, and in use, the light is reflected off the soil adjacent to the window. A spectrometer in spectroscopy assembly 14 then measures and records the spectra of the reflected light, which may also be referred to as diffuse reflectance spectra. The recorded spectra are then analyzed for the overtone wavelengths of the salts of fatty acids 22, as discussed elsewhere herein. Spectroscopy assembly 14 generally includes an onboard computer utilizing software capable of measuring and recording the spectra.

Spectroscopy assembly 14 may include a mobile delivery vehicle that houses the spectroscopy probe 16. Spectroscopy assembly 14 may include a hydraulic system for pushing the spectroscopy probe 16 into the ground.

Exemplary spectroscopy assemblies 14 and aspects thereof are disclosed in U.S. Pat. Nos. 5,038,040; 5,461,229; and 9,285,501, which are each incorporated herein by reference. An exemplary spectroscopy assembly 14 is sold by Veris Technologies, Inc. under the trade name Veris P4000.

As suggested above, spectroscopy assembly 14 should be particularly adapted to locate a decay product of human decomposition 24, e.g. salts of fatty acids 22. These decay products may be found based on certain wavelengths recorded by the spectroscopy assembly 14.

For example, it has been found that the salts of fatty acids 22 can be characterized by certain overtone wavelengths. Advantageously, spectroscopy assembly 14 may be particularly configured to identify the salts of fatty acids 22 within the location 12 that may include human remains based on these certain overtone wavelengths.

In one or more embodiments, these overtone wavelengths can be characterized by an absorption band contour extending from about 1670 nm to about 1780 nm, in other embodiments, from about 1670 nm to about 1800 nm. The absorption band contour generally includes two regions of increased area extending to respective peak absorption wavelengths.

In one or more embodiments, the peak absorption wavelengths for the overtone bands of the salts of fatty acids 22 have been measured at 1731 nm and 1763 nm, with an approximate uncertainty of +/−1 nm for each wavelength. That is, in one or more embodiments, these peak absorption wavelengths for the overtone bands of the salts of fatty acids 22 may be referred to as being between 1730-1732 nm and between 1762-1764 nm. In other embodiments, the approximate uncertainty for each wavelength may be +/−2 nm, such that these peak absorption wavelengths of the salts of fatty acids 22 may be referred to as being between 1729-1733 nm and between 1761-1765 nm.

Figure 2:
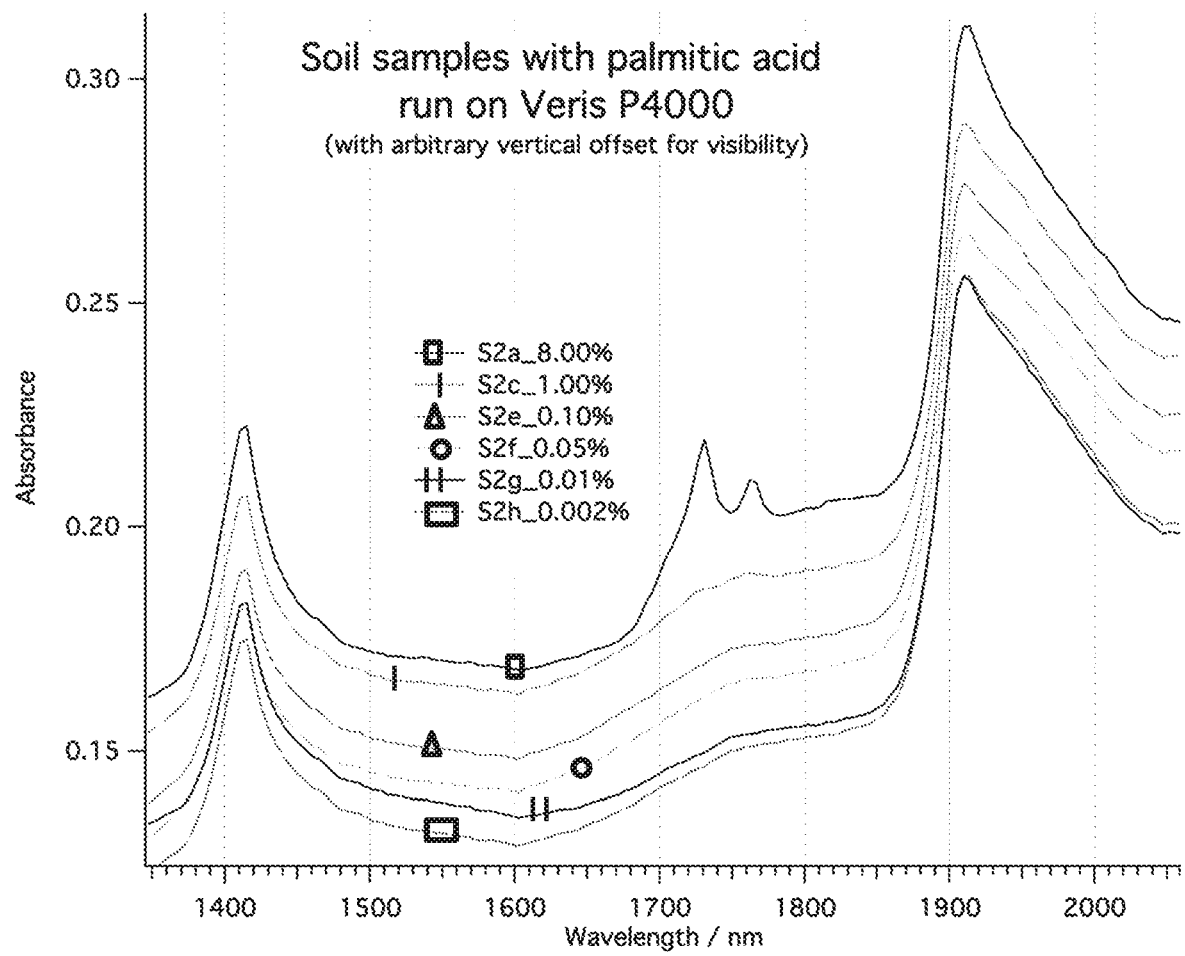
FIG. 2 is a graph showing spectra from soil samples spiked with palmitic acid.
Figure 3:
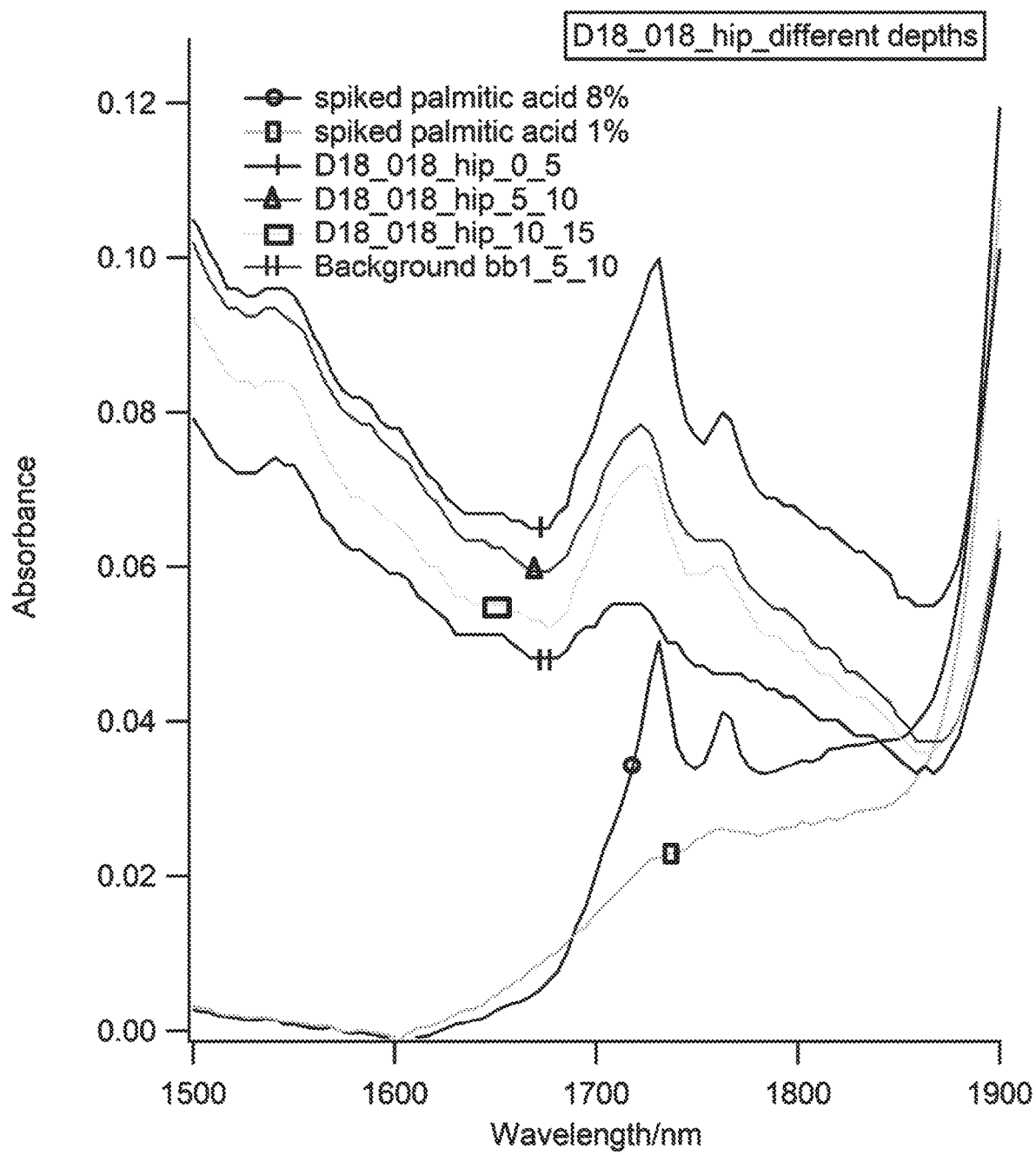
FIG. 3 is a graph showing spectra from a variety of soil samples.

One skilled in the art will readily understand that the above wavelengths serve to identify the absorption band profiles such as shown in FIG. 2 and FIG. 3.

In one or more embodiments, the spectroscopy assembly 14 and the corresponding method are configured to only identify whether a salt of a fatty acid is present based on these overtone wavelengths of the salt of the fatty acid. In one or more embodiments, the spectroscopy assembly 14 and the corresponding method are configured to consist essentially of identifying whether a salt of a fatty acid is present based on these overtone wavelengths of the salt of the fatty acid.

Generally speaking, the spectra of these overtone wavelengths indicate weak intensity. Thus, even based on the teachings of the prior art, it was surprising that these overtone wavelengths could have led to the methods disclosed herein of locating human remains in clandestine or undocumented burials.

As generally understood by the skilled person, spectroscopy assembly 14 may undergo a calibration step prior to use. This calibration step may be particularly adapted in accord with the location of a decay product of human decomposition 24 and identification thereof, as discussed herein. Other aspects related to calibration are disclosed in U.S. Pat. No. 9,285,501, which is incorporated herein by reference.

There are a variety of factors that may lead to the identification of a particular location 12 that may include human remains. Exemplary locations 12 include those locations where war events have occurred and locations where a criminal may have buried human remains. The identification of a particular location 12 that may include human remains may be driven by other forensics factors. These forensics factors may include the assistance of police and military investigators to develop a lead based on witness testimony and the history of the crime or conflict.

The location 12 that may include human remains includes a testing spot 28A where the spectroscopy probe 16 is to be inserted. The location 12 that may include human remains may also include a plurality of testing spots (i.e. testing spot 28A and testing spot 28B) where the spectroscopy probe 16 is to be inserted.

It is generally desirable to utilize a plurality of testing spots 28A, 28B for precise understanding of whether location 12 includes human remains. These plurality of testing spots 28A, 28B may be characterized by the distance between the testing spots 28A, 28B. In one or more embodiments, the distance between each testing spot 28A, 28B is from 5 cm to 100 cm, in other embodiments, from 10 cm to 50 cm, in other embodiments, from 10 cm to 20 cm, and in other embodiments, from 25 cm to 50 cm. In one or more embodiments, the average distance between each testing spot 28A, 28B is about 100 cm, in other embodiments, about 50 cm, in other embodiments, about 25 cm, and in other embodiments, about 10 cm. In one or more embodiments, the distance between each testing spot 28A, 28B is at least 10 cm, in other embodiments, at least 20 cm, in other embodiments, at least 25 cm, and in other embodiments, at least 50 cm. In one or more embodiments, the distance between each testing spot 28A, 28B is less than 200 cm, in other embodiments, less than 100 cm, and in other embodiments, less than 50 cm.

The plurality of testing spots 28A, 28B may be tested at a certain depth. Measuring at depths that are too near ground level 20 may lead to possible confusion of human remains 24 with other ubiquitous materials. For example, a false positive may be possible if someone had buried a family pet or fatty residue within the search area, and if the testing depth is not deep enough to get beyond these false results. Also, wild animal remains are generally found on the surface, not buried underground, so they would not cause a false positive indication.

In one or more embodiments, the depth of each testing spot 28A, 28B is from 20 cm to 150 cm, in other embodiments, from 30 cm to 90 cm, in other embodiments, from 40 cm to 80 cm, and in other embodiments, from 45 cm to 70 cm. In one or more embodiments, the average depth of each testing spot 28A, 28B is about 100 cm, in other embodiments, about 80 cm, in other embodiments, about 60 cm, and in other embodiments, about 45 cm. In one or more embodiments, the depth of each testing spot 28A, 28B is at least 30 cm, in other embodiments, at least 50 cm, in other embodiments, at least 70 cm, and in other embodiments, at least 100 cm. In one or more embodiments, the depth of each testing spot 28A, 28B is less than 200 cm, in other embodiments, less than 100 cm, and in other embodiments, less than 70 cm.

The location 12 that may include human remains may be characterized by one or more properties of the soil thereof. Soil generally has characteristic water absorption peaks near 1920 nm and near 1420 nm. These are broad peaks that become much more intense in wet soils, so much so that the relevant fatty acid peaks discussed elsewhere herein are tiny bumps in the rounded valley between these two giant peaks.

If the soil of location 12 includes fatty content in the naturally occurring organic matter contained within the soil, a false positive may be possible; that is, if the method disclosed herein is not performed. This background 'false positive' is generally shown in the "Background" sample of FIG. 3. Certain organic compounds not resulting from human remains have absorption bands in the same region of the spectrum as those resulting from human remains. Examples of these other organic compounds include kitchen waste and residues derived from petroleum. In general, such materials will have slightly different absorption band contours, such that they might be distinguished from the fatty acid salts characteristic of human remains, as discussed elsewhere herein. These false positives, and other false negatives, can also be mitigated by performing the secondary indicators discussed elsewhere herein.

As suggested above, the method 10 generally includes focusing on identifying fatty acids 22, by way of the salts of those fatty acids. Fatty acids 22 are constituents of adipocere, which is a decay product of human decomposition 24, which may also be referred to as human remains 24. The fatty acids 22, for example, palmitic acid, myristic acid, oleic acid, and stearic acid, are believed to primarily be in the form of a salt or salts of the fatty acid. The salt of the fatty acid 22 may be referred to herein simply as fatty acids 22 inasmuch as the fatty acid component of the salt will be detected by the spectroscopy assembly 14.

The salts of fatty acids 22 are formed with the metals generally found in the ground. Exemplary metals include alkaline earth metals such as calcium and magnesium. These salts of fatty acids 22 may persist in the soil location 12 for many years, up to decades or even centuries.

The analysis as to the presence or absence of these fatty acids 22 based on their certain overtone wavelengths may include an analysis as to the amount of the fatty acids 22. FIG. 2 and FIG. 3 generally show that higher amounts of fatty acids 22 lead to larger absorption peaks as indicated by their height above a baseline. Thus, the size of these peaks might be utilized to determine how close any particular testing spot 28A, 28B is to human remains 24. For example, if first testing spot 28A has a larger peak than second testing spot 28B, this may be an indication that human remains 24 are closer to first testing spot 28A.

Similarly, as suggested above, the analysis as to the presence or absence of these fatty acids 22 based on their certain overtone wavelengths may include an analysis as to the type of the fatty acids 22. The contour of these peaks might be utilized to determine the original source of the fatty acids 22. For example, a certain contour may indicate fatty acids 22 from human remains 24 whereas a different contour may indicate fatty acids from another source of fat, such as kitchen waste.

In one or more embodiments, the concentration of fatty acids 22 within the soil may be in a range of from about 6% to about 10%. Lower concentrations may also be detectable. In other embodiments, where the analysis is directly in a location including adipocere, the concentration of fatty acids 22 may be up to 80%.

As suggested above, by obtaining information about nearby location 26 near the location that may include human remains, where the nearby location 26 does not include human remains, further conclusions may be drawn. This may also be referred to as obtaining secondary properties or secondary indicators from the nearby location 26. Nearby location 26 may be one location or a plurality of locations. In embodiments where a plurality of locations are utilized for nearby location 26, this may provide a good measure of the background soil conditions may be obtained and serve to define the 'baseline' spectrum.

In or more embodiments, nearby location 26 includes a plurality of locations within 1 meter to 10 meters of the location 12 that may include human remains.

Exemplary secondary properties or indicators may include measurements by equipment that indicates the presence of a refilled excavation, for example, a grave excavation. This indication would tend to indicate the presence of human remains 24. Particular secondary property measurements include probe insertion pressure, variation of the soil color, and variations in water retention. Obtaining these secondary properties or indicators can cut down on false negatives; that is, those instances where human remains are at location 12 but initial testing does not find the human remains.

Regarding probe insertion pressure, a lower probe insertion pressure generally indicates the location of a refilled excavation. That is, location 12 that may include human remains will generally have a lower probe insertion pressure than nearby location 26. In one or more embodiments, location 12 that may include human remains may have probe insertion pressure that is about 30%, in other embodiments, about 50%, and in other embodiments, about 70%, of the probe insertion pressure at nearby location 26. These pressure values may be taken at an insertion depth of from 20 cm to 80 cm, for example, at about 50 cm.

Regarding soil color, the soil color may reflect the mixing of the darker topsoil deeper into the ground. That is, location 12 that may include human remains will generally have a darker soil color than nearby location 26. These soil colors may be taken at an insertion depth of from 20 cm to 80 cm, for example, at about 50 cm.

In addition to any advantages discussed above, the present methods may offer one or more other advantages. The present methods may offer a success rate of greater than 80%, and in other embodiments, greater than 90%, per excavation. Certain prior art techniques have a success rate of less than 30% per excavation. The present methods may also offer an improved recovery rate compared to prior art techniques. Certain prior art techniques have a recovery rate of about 3%.

As should be appreciated by one of ordinary skill in the art, the present invention offers an improvement in the technology of utilizing spectroscopy. Moreover, the utilization of the spectroscopy assembly and spectroscopy probe should be considered a practical application as to certain aspects discussed herein.

In light of the foregoing, it should be appreciated that the present invention significantly advances the art by providing an improved method of locating human remains in clandestine or undocumented burials. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following particular Examples are provided.

Example Shown in FIG. 2

FIG. 2 includes spectra obtained from a variety of soil samples that were dosed with varying amounts of palmitic acid, with the amounts identified in FIG. 2. In the 8% palmitic acid sample, the palmitic acid peaks are easily visible at 1731 nm and 1762 nm. These peaks are still discernible in the 1% palmitic acid sample, but not in the 0.1% palmitic acid sample.

Example Shown in FIG. 3

FIG. 3 includes spectra obtained from a variety of soil samples. Two of the samples were dosed with palmitic acid at amounts of 8% and 1%. Three of the samples (labeled D18_018) were taken from different spots at a site including a human cadaver. In these three samples, the palmitic acid peaks are visible at about 1731 nm and about 1762 nm. One of the samples (labeled background) was taken near the site including the human cadaver from a spot that did not include the human cadaver.

What is claimed is:

1. A method for locating human remains in a clandestine or undocumented burial, the method comprising:
    identifying a location that includes human remains, where the location that includes human remains includes a fatty acid deriving from adipocere, where the adipocere is a decay product of decomposition of the human remains, where the fatty acid is in the form of a salt of the fatty acid;
    providing a spectroscopy assembly including a spectroscopy probe with a distal end to the location that includes human remains, wherein the spectroscopy assembly is configured to identify whether the salt of the fatty acid is present based on overtone wavelengths of the salt of the fatty acid;
    inserting the distal end of the spectroscopy probe into a testing spot at the location that includes human remains; and
    analyzing, with the spectroscopy assembly and after the step of inserting, presence of the salt of the fatty acid having the overtone wavelengths in the location that includes human remains, wherein the step of analyzing includes utilizing near-infrared spectroscopy.

2. A method for locating human remains in a clandestine or undocumented burial, the method comprising:
    identifying a location that may include human remains;
    providing a spectroscopy assembly including a spectroscopy probe with a distal end to the location that may include human remains, wherein the spectroscopy assembly is configured to identify whether a salt of a fatty acid is present based on overtone wavelengths of the salt of the fatty acid, wherein the overtone wavelengths are characterized by an absorption band contour extending from about 1670 nm to about 1800;
    inserting the distal end of the spectroscopy probe into a testing spot at the location that may include human remains; and
    analyzing, with the spectroscopy assembly and after the step of inserting, whether the salt of the fatty acid having the overtone wavelengths is present in the location that may include human remains, wherein the step of analyzing includes utilizing near-infrared spectroscopy.

3. The method of claim 2, wherein the absorption band contour includes a first peak absorption wavelength of from 1729 nm to 1733 nm and a second peak absorption wavelength of from 1761 nm to 1765 nm.

4. The method of claim 2, wherein the absorption band contour includes a first peak absorption wavelength of from 1730 nm to 1732 nm and a second peak absorption wavelength of from 1762 nm to 1764 nm.

5. The method of claim 4, further comprising steps of
measuring a secondary property of the location that may include human remains;
measuring the secondary property for a plurality of nearby locations near the location that may include human remains, wherein the plurality of nearby locations do not include human remains; and
comparing the secondary property of the location that may include human remains with the secondary property of the plurality of nearby locations.

6. The method of claim 5, wherein the step of comparing is suitable for eliminating any false negative conclusion from the step analyzing, to thereby provide further conclusive results as to whether any fatty acids or salts of fatty acids are present in the location that may include human remains.

7. The method of claim 5, wherein the secondary property is probe insertion pressure.

8. The method of claim 7, wherein the location that may include human remains has a lower probe insertion pressure than the nearby location.

9. The method of claim 5, wherein the secondary property is soil color.

10. The method of claim 9, wherein the location that may include human remains has a darker soil color than the nearby location measured at a depth of 50 cm.

11. The method of claim 5, wherein the secondary property is water retention.

12. The method of claim 5, wherein the plurality of nearby locations are each within 1 meter to 10 meters of the location that may include human remains.

13. The method of claim 4, wherein the salt of the fatty acid is an alkaline earth metal salt.

14. The method of claim 13, wherein the alkaline earth metal salt is calcium or magnesium.

15. The method of claim 14, wherein the fatty acid of the salt of the fatty acid is selected from the group consisting of palmitic acid, myristic acid, oleic acid, and stearic acid.

16. The method of claim 4, wherein the location that may include human remains is a location where war events have occurred or a location where a criminal is believed to have buried human remains, wherein the location that may include human remains includes a plurality of the testing spots, wherein the steps of inserting and analyzing are repeated for each of the plurality of the testing spots.

17. The method of claim 16, wherein the plurality of the testing spots are at a depth of from 20 cm to 150 cm.

18. The method of claim 16, wherein the plurality of the testing spots are at an average depth of about 60 cm.

19. The method of claim 16, wherein the distance between the plurality of the testing spots is from 5 cm to 100 cm.

20. The method of claim 16, wherein the average distance between the plurality of the testing spots is about 50 cm.

* * * * *